United States Patent
Ohtomo

[19]

[11] Patent Number: 5,817,018
[45] Date of Patent: *Oct. 6, 1998

[54] METHOD FOR MEASURING SPEED OF SOUND IN TISSUE AND TISSUE ASSESSMENT APPARATUS

[75] Inventor: Naoki Ohtomo, Mitaka, Japan

[73] Assignee: Aloka Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 786,967

[22] Filed: Jan. 27, 1997

Related U.S. Application Data

[62] Division of Ser. No. 576,682, Dec. 21, 1995, Pat. No. 5,615,681.

[30] Foreign Application Priority Data

Dec. 22, 1994 [JP] Japan .................................. 6-319721

[51] Int. Cl.$^6$ ...................................................... A61B 8/00
[52] U.S. Cl. ............................................. 600/437; 600/437
[58] Field of Search ........................ 128/660.01, 660.02, 128/660.06, 661.03; 600/437, 439, 449

[56] References Cited

U.S. PATENT DOCUMENTS

| | | |
|---|---|---|
| 2,439,130 | 4/1948 | Firestone . |
| 3,345,863 | 10/1967 | Henry et al. . |
| 3,477,422 | 11/1969 | Jurist, Jr. et al. . |
| 3,587,561 | 6/1971 | Ziedonis . |
| 3,648,685 | 3/1972 | Hepp et al. . |
| 3,664,180 | 5/1972 | McDonald et al. . |
| 3,711,129 | 1/1973 | Smathers et al. . |
| 3,713,329 | 1/1973 | Munger . |
| 3,782,177 | 1/1974 | Hoop . |
| 3,847,141 | 11/1974 | Hoop . |
| 4,048,986 | 9/1977 | Ott . |
| 4,056,970 | 11/1977 | Sollish . |
| 4,235,243 | 11/1980 | Saha . |
| 4,361,154 | 11/1982 | Pratt, Jr. . |
| 4,393,712 | 7/1983 | Sandhu . |
| 4,421,119 | 12/1983 | Pratt, Jr. . |
| 4,476,873 | 10/1984 | Sorenson et al. . |
| 4,522,068 | 6/1985 | Smith . |
| 4,530,360 | 7/1985 | Duarte . |
| 4,567,747 | 2/1986 | Matay .......................................... 73/1 |
| 4,774,959 | 10/1988 | Palmer et al. . |

(List continued on next page.)

FOREIGN PATENT DOCUMENTS

| | | |
|---|---|---|
| A-0 341 969 | 11/1989 | European Pat. Off. . |
| A-0 576 217 | 12/1993 | European Pat. Off. . |
| WO-A-87 07494 | 12/1987 | WIPO . |

OTHER PUBLICATIONS

European Search Report Communication dated May 29, 1996.

*Primary Examiner*—Francis Jaworski
*Attorney, Agent, or Firm*—Fish & Richardson, PC

[57] ABSTRACT

A method for measuring the speed of sound in a tissue such as bone. First, the transducer covers of a pair of transducer units are pressed together under a predetermined pressure, ultrasound is transmitted and received, and the time taken by the ultrasound to travel from one to the other of the transducers is measured. Next, the tissue is held between the pair of transducer units under the same predetermined pressure, ultrasound is transmitted and received, the time taken for the ultrasound to travel from one to the other of the transducers is measured, and the distance between the two transducers is measured. The speed of sound in the tissue is then computed based on the propagation time of ultrasound when the transducer units are directly pressed together, the propagation time of ultrasound and the distance between the transducers when the tissue is held between the pair of transducer units. By this method, an accurate value for the speed of sound in the tissue unaffected by changes in the properties of the acoustic matching material filling the transducer covers, can be computed.

5 Claims, 12 Drawing Sheets

U.S. PATENT DOCUMENTS

| | | | |
|---|---|---|---|
| 4,926,870 | 5/1990 | Brandenburger . | |
| 4,941,474 | 7/1990 | Pratt, Jr. | 128/660.01 |
| 5,042,489 | 8/1991 | Wiener et al. . | |
| 5,054,490 | 10/1991 | Rossman et al. | 128/661.03 |
| 5,203,333 | 4/1993 | Nomura | 601/4 X |
| 5,335,661 | 8/1994 | Koblanski | 128/661.03 |
| 5,343,863 | 9/1994 | Wiener et al. . | |
| 5,348,009 | 9/1994 | Ohtomo et al. | 128/660.01 |
| 5,452,722 | 9/1995 | Langton | 128/660.06 |

METHOD FOR MEASURING SPEED OF SOUND IN TISSUE AND TISSUE ASSESSMENT APPARATUS

This application is a divisional of U.S. application Ser. No. 08/576,682, filed Dec. 21, 1995, now U.S. Pat. No. 5,615,681.

BACKGROUND OF THE INVENTION:

1. Field of the Invention

This invention relates to a tissue assessment apparatus for assessing the state of tissue such as bone using ultrasound, and in particular, to measurement of the speed of ultrasound propagated in tissue.

2. Description of the Related Art

In a tissue measurement apparatus using ultrasound, ultrasound is transmitted to a part of an organism (e.g. the heel), and the ultrasound which has passed through or been reflected by the organism is received. Based on a signal obtained from the received ultrasound, the speed of sound in the tissue or the degree of attenuation of the ultrasound by the tissue is computed as an indicator of the state of the tissue. An example of such an apparatus is a bone assessment apparatus used to examine for example the heel bone or calcaneous. In addition to tissue assessment apparatuses using only ultrasound, moreover, other apparatuses using both ultrasound and X rays have been proposed.

It is however known that when a tissue assessment is performed by means of ultrasound, it is impossible to obtain a precise measurement or assessment of speed or attenuation of ultrasound when an air layer is present in the path from the transmitting ultrasound transducer to the receiving ultrasound transducer. This is due to the fact that the ultrasound is reflected or attenuated by the air layer. In order to eliminate the air layer which interferes with ultrasonic examinations, therefore, the sample (tissue) and ultrasonic transducers were conventionally immersed in a measuring bath containing an acoustic matching material such as water, and predetermined measurements were carried out by transmitting and receiving the ultrasound through this material.

However, in the method where the sample was immersed in an acoustic matching material, the subject occasionally experienced discomfort, and it was difficult to ensure that the procedure of measurement was hygienic.

In Japanese Patent Application No. HEI-6-7010 (Japanese Patent Laid-Open No. HEI-7-204205), the Applicant proposes a tissue assessment apparatus which resolves these problems. In this apparatus, the front of the ultrasonic transducer is covered with a cover (or membrane) that can deform, the cover is filled with an acoustic matching material, and the cover is brought in contact with the sample. In other words, the sample is gripped between two ultrasonic transducers facing each other, and the propagation time of the ultrasound between the both transducers is measured. The propagation speed of the ultrasound in the sample, i.e. in the tissue, is then found by dividing the distance between the transducers by the propagation time. According to this method, the deformable cover easily comes into contact with the surface of the sample, so no air layer is present between the transducers and the sample.

In this art, however, a problem arises in that when the surrounding conditions, in particular the temperature or air pressure change during a measurement, the properties of the acoustic matching material also change and give rise to errors in measured values.

In this art, the distance used to compute speed of sound in the sample tissue comprises the thickness of the acoustic matching material, and the time used to compute speed of sound in the sample tissue comprises the time required for ultrasound to propagate through the acoustic matching material. Hence even for the same sample, if the properties of the matching material change due to a change in the measuring conditions, the value of speed of sound obtained may be different. Further, if there is an error in the speed of sound, there is a possibility of an error arising in other assessment values computed from the speed of sound.

When for example castor oil is used as the acoustic matching material and the temperature of the oil changes by 1° C. in the vicinity of room temperature, the speed of sound in the oil changes by approx. 3 m/s. Therefore, when for example the thickness of castor oil is approx. 4 cm and the thickness of the sample is approx. 6 cm in the aforesaid apparatus, and the oil temperature changes by 1° C., an error of about 1.2 m/s arises in the measured result for the speed of sound in the sample.

If an air cell becomes mixed with the acoustic matching material in the cover of the aforesaid apparatus, further problems arise. In this case, when the atmospheric pressure of the measuring environment changes, the air cell expands or contracts. The deformation of the cover pressing on the sample therefore changes due to the atmospheric pressure, and the average thickness of the acoustic matching material changes as a result. This leads to errors in the measured value of the speed of sound.

The thickness of the acoustic matching material also changes if the material leaks out of the cover due to long periods of use.

The part of the cover in contact with the tissue has excellent transparency to ultrasound and is formed of a thin film such as a polyurethane sheet which is highly flexible. When used for long periods however, the flexibility of the cover changes, so the degree to which the cover is deformed changes even when pressed against the sample by the same pressure. This also causes the thickness of the acoustic matching material to vary, and leads to errors in the measured result for the speed of sound.

In general, the speed of sound in the acoustic matching material and in the sample tissue are not the same, hence when the average thickness of the material changed due to a variation of environmental conditions, long periods of use or a change in the flexibility of the cover in the aforesaid technique, there was a risk that a different result would be obtained for the speed of sound even if the same sample were measured.

SUMMARY OF THE INVENTION

This invention was conceived in view of the aforesaid problems. It aims to provide a method and apparatus for measuring the speed or velocity of sound in tissue which always gives an accurate result for the speed of sound regardless of the environmental conditions.

In order to achieve the aforesaid object, the method of measuring the speed of sound according to this invention comprises the following steps:

(a) a preparing step wherein a pair of transducer unit covers are pressed together under a predetermined pressure, ultrasound is transmitted and received, and the propagation time of the ultrasound from one transducer to the other is measured, (b) a measuring step wherein a tissue is held between the aforesaid pair of transducer units under the aforesaid predetermined pressure, ultrasound is transmitted and received, the propagation time of the ultrasound from one transducer to the other is measured, and the distance between the two transducers is also measured, and (c) a calculating step wherein the speed of sound in the tissue is computed based on the propagation time measured in the preparing step, the propagation time measured in the measuring step and the distance between the transducers.

According to this method, the time required for the ultrasound to propagate through only the tissue may be found from the propagation time calculated in step (a) and the propagation time calculated in step (b). In this method, the speed of sound is based on this time and the distance between the transducers found in (b), hence an accurate speed may be calculated which is unaffected by the state of the acoustic matching material.

According to this method, the speed of sound in the tissue may also be found from the speed of sound in the matching material in step (b), the propagation time measured in step (a), and the propagation time and distance between transducers measured in step (b). This corrects for temperature differences of the acoustic matching material between step (a) and step (b) so that an even more accurate value for the speed of sound in tissue may be found.

The sound speed measuring method of this invention comprises the following steps:

(a) a preparing step wherein a reference phantom having a predetermined thickness is held between a pair of transducer units under a predetermined pressure, ultrasound is transmitted and received, the propagation time of the ultrasound from one transducer to the other is measured, and the temperature of the reference phantom is also measured, (b) a step for calculating speed of sound in the aforesaid reference phantom based on the temperature of the reference phantom, (c) a measuring step wherein a tissue is held between the aforesaid pair of transducer units under the aforesaid predetermined pressure, ultrasound is transmitted and received, the propagation time of the ultrasound from one transducer to the other transducer is measured, and the distance between two transducers is measured, and (d) a calculating step for computing the speed of sound in a tissue based on the propagation time measured in the preparing step, the propagation time and distance between transducers measured in the measuring step, and the speed of sound in the aforesaid reference phantom.

In this method, in step (a), a reference phantom of a predetermined thickness is held between the transducers, and the distance between transducers is measured.

The distance between transducers may for example be measured by means of a laser range finder. In general, an effective length measurement range is specified for laser range finders. Therefore, if there were a large difference in the inter-transducer distance measured in steps (a) and step (c), two types of laser range finder would be required making the equipment more complex and costly.

According to this method, however, a reference phantom which is as thick as the tissue is used in step (a), hence an economical laser range finder having a small effective length measurement range may be used.

The tissue assessment apparatus according to this invention comprises the following elements:

A pair of transducer units, each unit comprising an ultrasonic transducer, a cover covering this transducer whereof at least part deforms freely, and an acoustic matching material filling the space between the transducer cover and the transducer, a transducer unit moving mechanism which moves the units closer towards or further apart from each other, a limiter which limits the force with which the transducer units are pressed against the tissue so as not to exceed a predetermined pressure when the pair of units hold the tissue, a memory for storing the propagation time of ultrasound between the transducers when the transducer covers of the units are pressed together at said predetermined pressure, a time measuring device which measures the propagation time of ultrasound between the transducers based on a signal received from the transducer units, a distance measuring device for measuring the distance between the transducers, and a processor for computing the speed of sound based on the propagation time stored in the memory, the propagation time found by the time measuring device and the distance measured by the distance measuring device.

According to this apparatus, the speed of sound in the tissue can be accurately measured based on the propagation time stored in the memory and the measurement results of various instruments without being affected by the state of the acoustic matching material.

DESCRIPTION OF THE PREFERRED EMBODIMENTS

Embodiment 1

Figure 1:
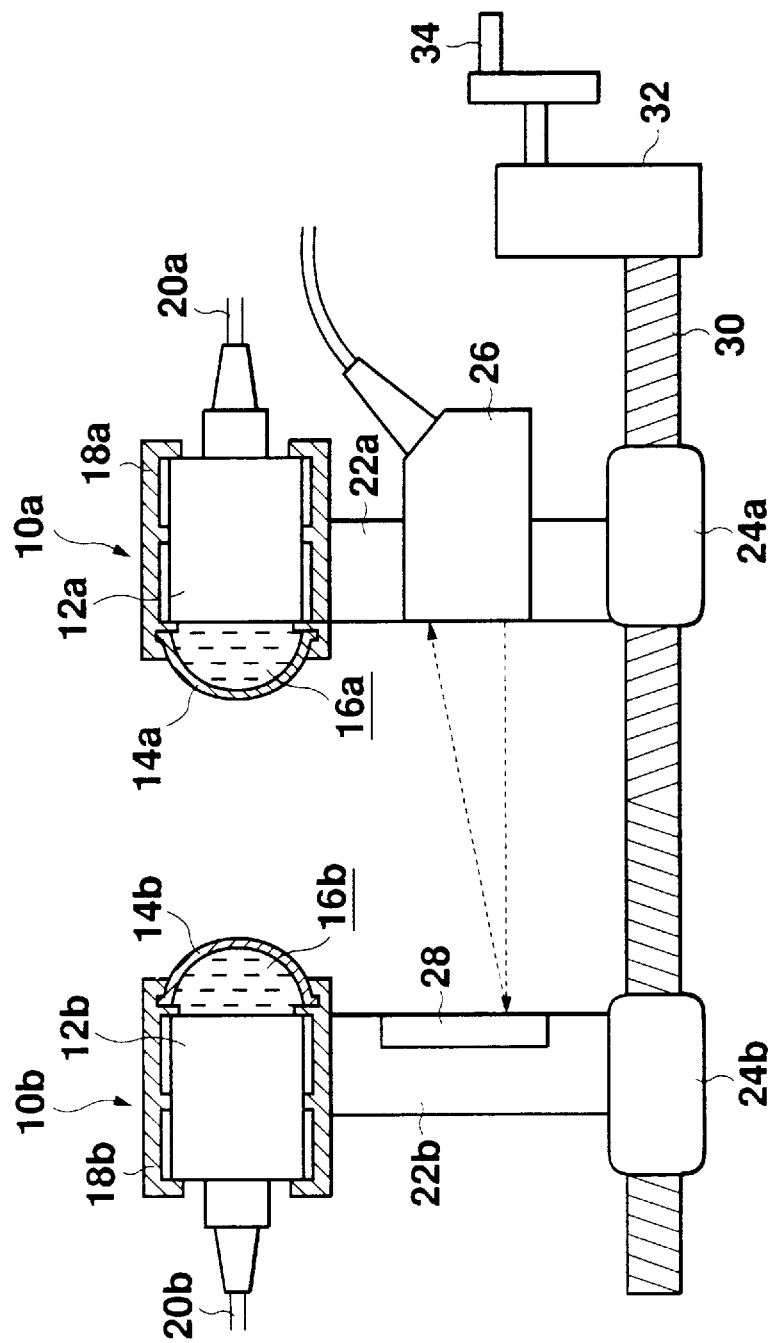
FIG. 1 is a diagram schematically showing a mechanical part of a tissue assessment apparatus according to this invention.

FIG. 1 is a diagram showing a typical mechanical construction of a tissue assessment apparatus according to this invention.

In FIG. 1, a pair of transducer units 10a, 10b are disposed such that ultrasonic transducers 12a,12b are facing each other. The transducers 12a, 12b are covered by transducer covers (or membranes) 14a, 14b each comprising a thin film which is flexible and transparent to ultrasound such as a polyurethane sheet. The spaces enclosed by the transducers 12a, 12b and the transducer membranes 14a, 14b are filled with acoustic matching materials 16a, 16b each comprising a liquid such as castor oil. Cords 20a, 20b lead off respectively from the rear ends of the transducers 12a, 12b. These cords 20a, 20b are connected to a transducer controller, not shown. The transducers 12a, 12b and the transducer covers 14a, 14b are housed in transducer cases 18a, 18b. These transducer cases 18a, 18b are respectively supported by arms 22a, 22b.

Nuts 24a, 24b that screw onto a feed screw 30 are disposed at the base ends of the arms 22a, 22b. When the feed screw 30 rotates, the arms 22a, 22b therefore move along the feed screw 30. The arms 22a, 22b either move closer together or further apart depending on the direction of rotation of the screw 30. In this way, the distance from the transducer unit 10a to the transducer unit 10b can be varied.

Hence, by rotating a wheel 34 so as to rotate the screw 30 in a predetermined direction, a sample such as a heel of a foot can be held between the pair of transducer units 10a, 10b. In the apparatus of FIG. 1, a torque limiter 32 is provided between the wheel 34 and screw 30, so even if an excessive force is applied to the wheel 34, the force transmitted to the screw 30 is always limited by the action of the torque limiter 32 so that it is equal to or less than a predetermined value. Due to the action of the torque limiter 32, application of an excessive force to the sample is avoided. A laser range finder 26 is also provided on the arm 22a, and a reflecting plate 28 that reflects a laser beam from the range finder 26 is provided on the arm 22b. The apparatus of FIG. 1, therefore, can measure the distance between the transducers 12a, 12b by means of the laser range finder 26.

Figure 2:
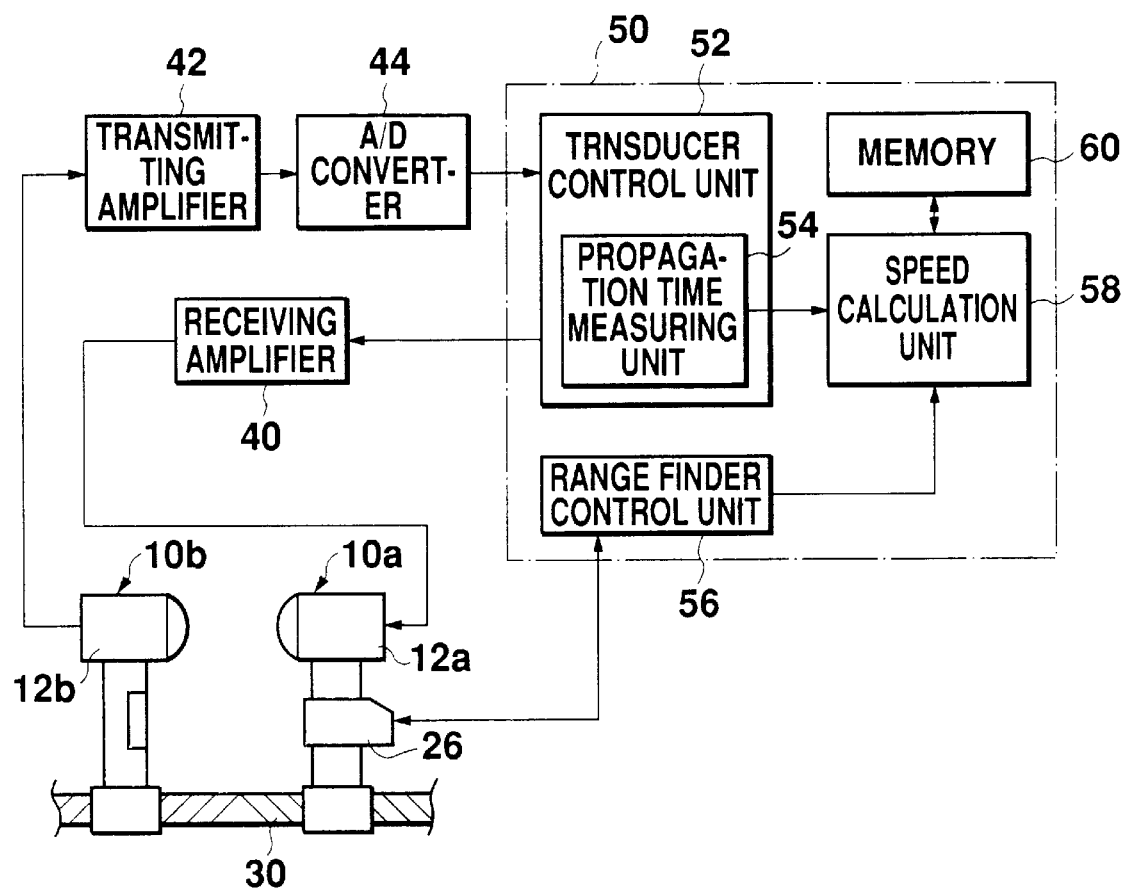
FIG. 2 is a block diagram showing the whole construction of the tissue assessment apparatus according to this invention.

FIG. 2 is a block diagram showing the whole construction of the apparatus according to this embodiment. In FIG. 2, parts identical to those of FIG. 1 are assigned the same symbols and their description is omitted.

In the figure, the transmitting transducer 12a is connected to a receiving amplifier 40, and the receiving transducer 12b is connected to a transmitting amplifier 42. The transmitting amplifier 42 is connected to an A/D converter 44. A transducer control unit 52 inside a controller 50 controls the receiving amplifier 40 so that ultrasound pulses are transmitted from the transducer 12a. The transducer control unit 52 receives a digitized signal from the A/D converter 44, and predetermined signal processing is performed on this received signal.

The action of the apparatus of FIG. 2 will now be described in further detail. First, the transducer control unit 52 sends a trigger pulse to the receiving amplifier 40. When the receiving amplifier 40 receives this trigger pulse, a predetermined drive pulse is generated and supplied to the transducer 12a. The transducer 12a is driven by this drive pulse supplied from the receiving amplifier 40, and emits ultrasound pulse. After this ultrasound pulse has passed through the sample, it is received by the transducer 12b. This weak received signal undergoes a predetermined amplification by the transmitting amplifier 42. The received signal after amplification is digitized by the A/D converter 44, and is supplied to the transducer control unit 52 inside the controller 50. The transducer control unit 52 comprises a propagation time measuring unit 54 which, using the trigger pulse timing, and the received signal, calculates the time required for the ultrasound to travel from the transducer 12a to the transducer 12b ("propagation time") according to a method known in the art. In addition to this propagation time, the transducer control unit 52 also calculates the degree of attenuation of the ultrasound using the received signal and other information.

The controller 50 comprises a range finder control unit 56. The range finder control unit 56 controls the laser range finder 26 so as to determine the distance between the transducers 12a, 12b.

The controller 50 further comprises a speed calculation unit 58 and a memory 60. The propagation time found by the propagation time measuring unit 54 and the transducer distance found by the range finder control unit 56 are input to the speed calculation unit 58. The speed calculation unit 58 calculates the speed of sound in the sample tissue using this input data. Intermediate data used in the calculation of speed of sound by the speed calculation unit 58 are stored in the memory 60. The speed of sound thus found is used as a value to assess the sample tissue, and used together with other assessment values to compute new assessment values.

A first embodiment of a method to measure speed of sound in a sample tissue by the apparatus shown in FIG. 1 and FIG. 2, will now be described.

Figure 3:
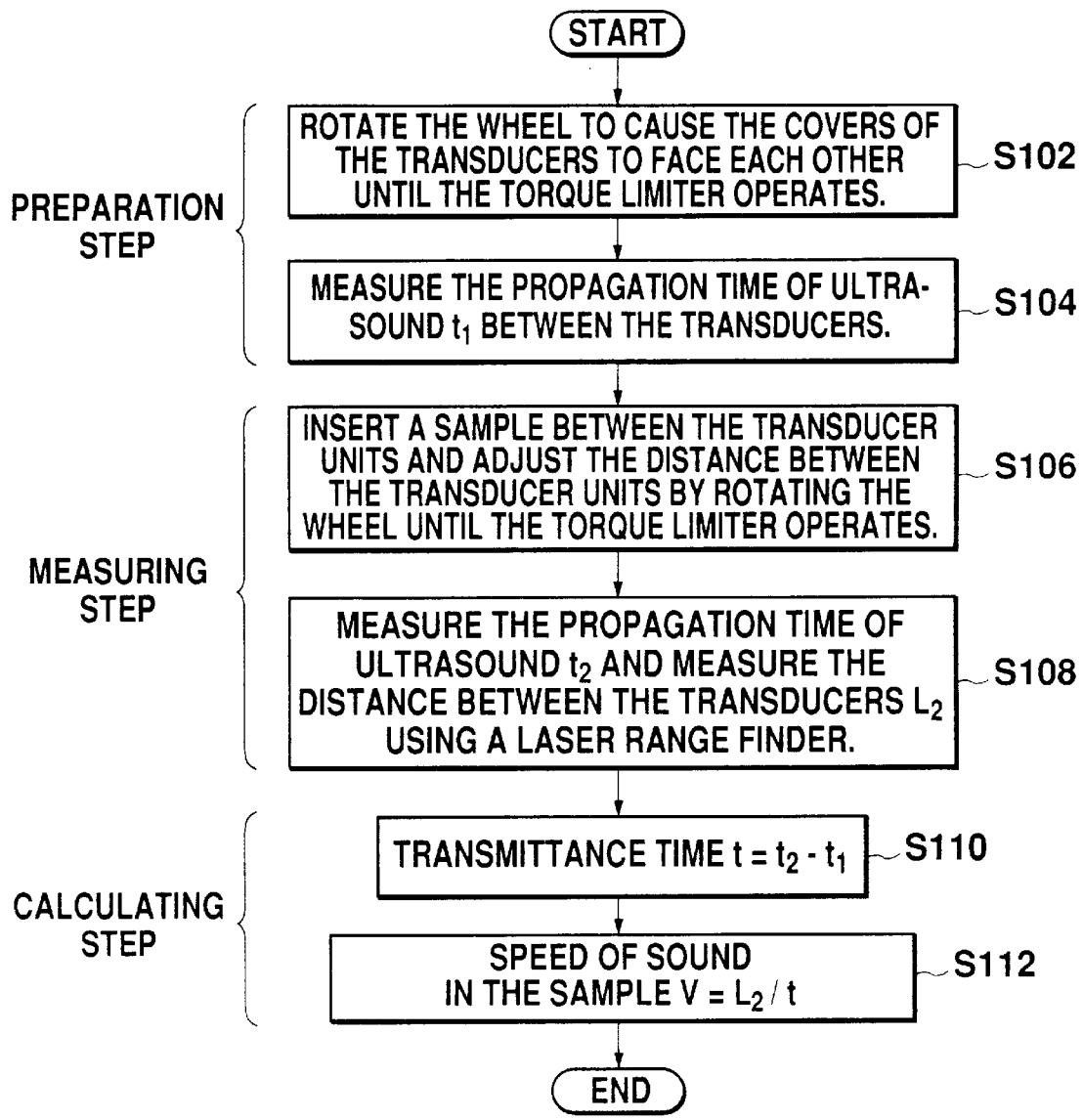
FIG. 3 is a flowchart showing a first embodiment of a method for measuring speed of sound in tissue.

FIG. 3 is a flowchart showing the method of the first embodiment.

As will be understood from the figure, the processing of the first embodiment may be broadly separated into three stages, i.e. a preparing step, a measuring step and a calculating step.

Figure 4:
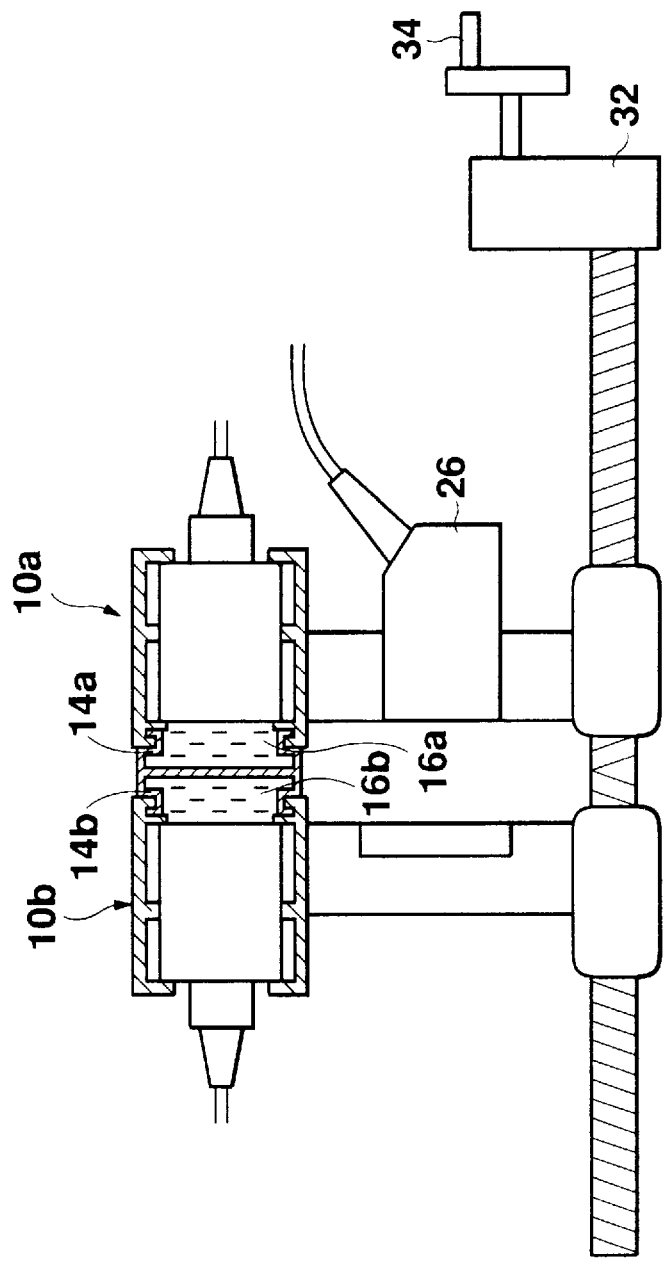
FIG. 4 is an illustrative diagram showing the state of the tissue assessment apparatus in a preparing step according to the first embodiment.

First, in the preparing step, an operator turns the wheel 34 so that the pair of transducer units 10a, 10b move closer together and the transducer covers (or membranes) 14a, 14b touch each other. The operator then increases the force applied to the wheel 34 until the torque limiter 32 operates, so that the transducer covers are pressed to each other with a predetermined force specified by the torque limiter 32 (S102). FIG. 4 shows the state of the apparatus of this embodiment at this time. As will be described hereinafter, when the sample is held between the transducer units in the measuring step, force is applied to the wheel 34 until the torque limiter 32 operates as in S102. Hence, as the force applied and maintained by the transducer units in the preparing step and the measuring step is substantially the same, the degree of deforming of the covers 14a, 14b, i.e. the thickness of the acoustic matching materials 16a, 16b, is also substantially the same.

Next, the propagation time $t_1$ of ultrasound between the transducers 12a, 12b is measured (S104). Ultrasound pulse is transmitted from the transducer 12a in the state shown in FIG. 4, and after passing through the acoustic matching materials 16a, 16b, the pulse is received by the transducer 12b. The propagation time $t_1$ of the ultrasound is calculated by the propagation time measuring unit 54 using the reception result. This propagation time $t_1$ is the time required for the ultrasound to travel through the acoustic matching material layers 16a, 16b, and it is input to the memory 60 via the speed calculation unit 58.

When measurement of the propagation time $t_1$ is completed, the operator rotates the wheel 34 in the opposite sense to that of the step S102 so as to temporarily widen the distance between the transducers.

Figure 5:
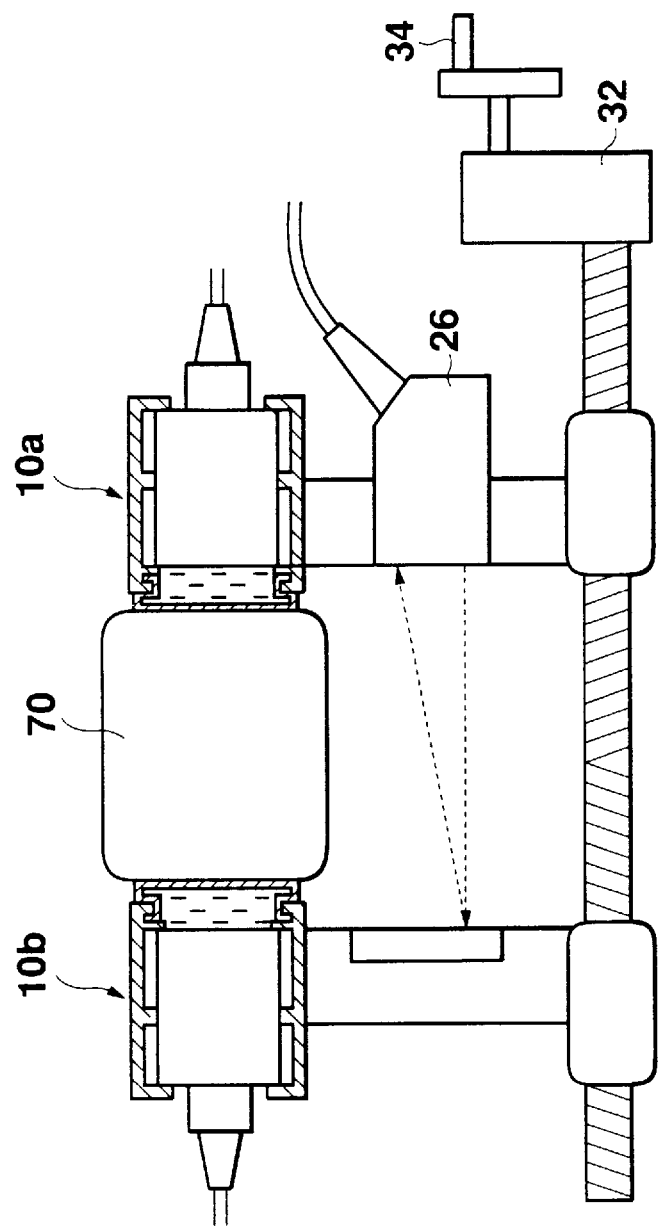
FIG. 5 is an illustrative diagram showing the state of the tissue assessment apparatus in a measuring step according to the first embodiment.

Next, in the measuring step as shown in FIG. 5, a sample 70 is disposed between the transducer units 10a, 10b. As in the step S102, the operator increases the force applied to the wheel 34 until the torque limiter 32 operates so as to press the transducer covers 14a, 14b against the sample 70 with a predetermined force specified by the torque limiter 32 (S106).

Next, ultrasound is transmitted and received in the state shown in FIG. 5, a propagation time $t_2$ of the ultrasound is measured, and simultaneously, the distance between the transducers 12a, 12b is measured using the laser range finder 26 (S108).

In the subsequent calculating step, a transmittance time t required for the ultrasound to travel through the sample 70 is first calculated from the propagation time $t_2$ of the measuring step found in the step S108 and the propagation time $t_1$ of the preparing step stored in the memory 60, using the following relation (S110):

$$t = t_2 - t_1 \quad (1)$$

According to this first embodiment, due to the use of the torque limiter, the pressure applied to the transducer covers (or membranes) and acoustic matching material layers is substantially the same in the preparing step and measuring step, consequently it may be considered that the thickness of the acoustic matching material is substantially the same in both steps. It may further be considered that the propagation time $t_1$ of the ultrasound in the acoustic matching material layer found in the preparing step, may be taken as the propagation time of the ultrasound in the acoustic matching material in the measuring step. By subtracting the propagation time $t_1$ found in the preparing step from the propagation time $t_2$ found in the measuring step, the time t required for the ultrasound to pass through the sample tissue may be found.

In this embodiment, using this transmittance time t and a transducer distance $L_2$ of the measuring step found in the step S108, the speed of sound V in the sample tissue may be found from the following relation (2) (S112):

$$V = L_2/t \quad (2)$$

According to the first embodiment, the propagation time $t_1$ in the acoustic matching material layer has been excluded from the speed of sound in the sample tissue. An accurate value V for the speed of sound in the sample tissue unaffected by variations of speed in the acoustic matching material due to temperature variations, may therefore be obtained.

The following method is a modification of the first embodiment.

Figure 6:
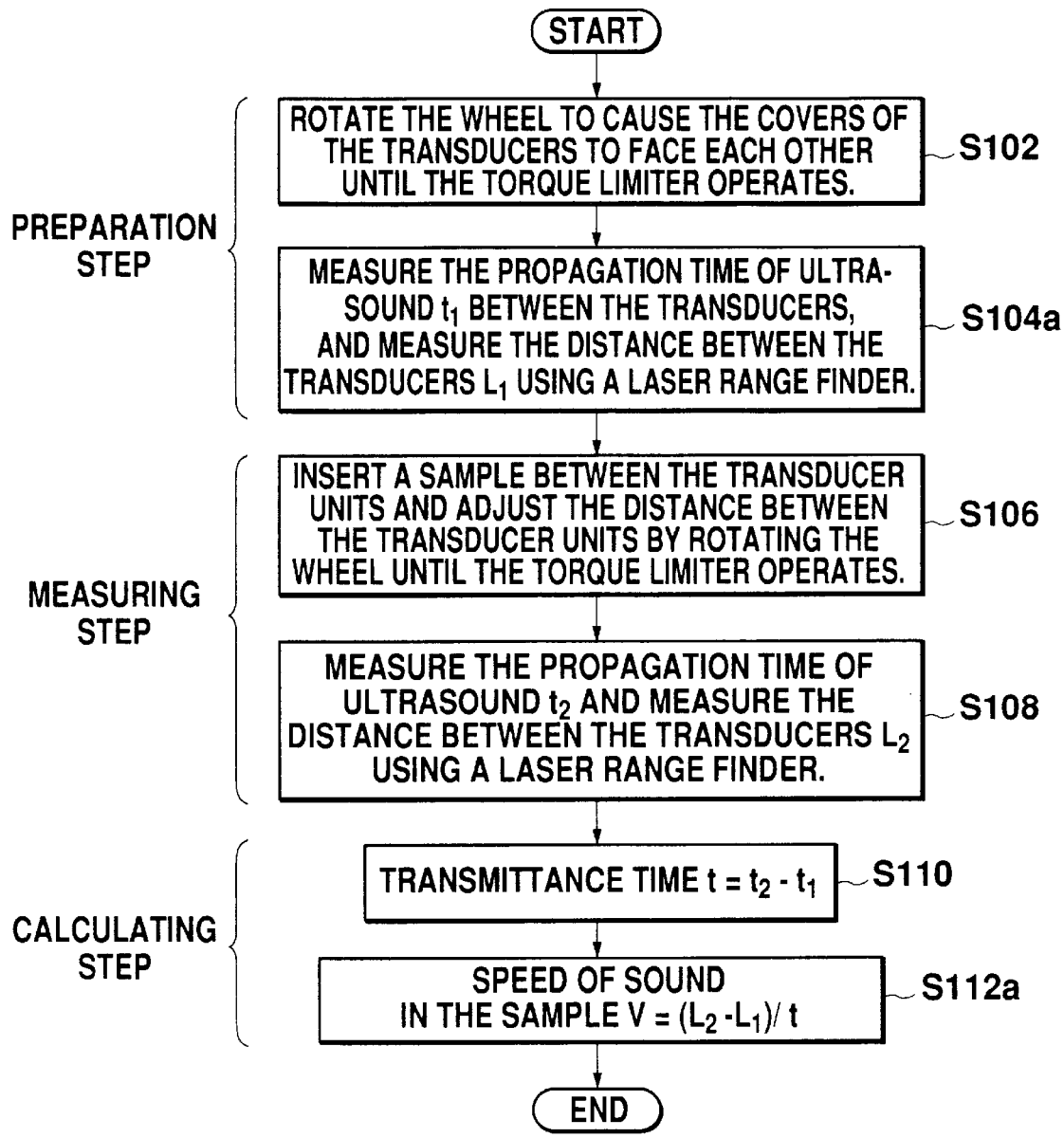
FIG. 6 is a flowchart showing a modification of the first embodiment.

FIG. 6 is a flowchart showing the processing performed in this modification. In FIG. 6, steps indicating the same processing as that of FIG. 3 are assigned the same symbols and their description is omitted. In this modification, a transducer distance $L_1$ is measured by the laser range finder 26 at the same time as the propagation time $t_1$ between the transducers is measured (S102a) in the preparing step. In the calculating step, the speed V of sound in the sample tissue is found by the following relation (2a) (S112a):

$$V = (L_2 - L_1)/t \quad (2a)$$

In this case, the transducer distance $L_1$ indicates the thickness of the acoustic matching material layer, so the thickness of the sample tissue alone may be found by subtracting $L_1$ from the transducer distance $L_2$. A more accurate value for the speed V of ultrasound in the sample tissue may then be found by dividing the thickness $(L_2 - L_1)$ of the sample tissue alone, by the time t required for the ultrasound to travel through the sample tissue alone.

The above is a description of the first embodiment and a modification of the first embodiment of this invention. The speed of sound V in the sample tissue found in this embodiment may itself be used as an assessment value of the sample tissue, or it may be used in conjunction with other assessment values to compute new assessment values. For example, ultrasound may be used in conjunction with X rays. A bone mineral density found by X ray measurement may be combined with the speed of sound determined according to this embodiment so as to compute the elastic modulus of the bone which may also be used as an assessment value.

According to this embodiment, a laser range finder was used to measure the transducer distance, however the invention is not limited to this arrangement, it being possible to use also mechanical means such as for example an encoder.

According to this embodiment, the transducer units were moved by turning the wheel 34, however the feed screw 30 may alternatively be turned by a motor so as to move the transducer units.

Herein a preparing step, measuring step and calculating step were described as being carried out sequentially, however it is not essential for the preparing step, measuring step (and calculating step) to be carried out in sequence. In other words, it is sufficient if the preparing step is performed regularly such as once a day or once a week. In this case, the propagation time $t_1$ and inter-transducer distance $L_1$ found in the preparing step are stored, only the measuring step being performed to examine different samples. It will of course be understood that the whole sequence of steps from the preparing step to the measuring step and calculating step, may also be performed when examining different samples.

Embodiment 2

Next, a second embodiment of the method of measuring the speed of sound in tissue according to this invention will be described. This second embodiment considers temperature variation of the acoustic matching materials 16a, 16b in order to find an even more precise value for the speed of sound in tissue.

In the measuring step, when the sample is held between the pair of transducers for a long period, the temperature of the acoustic matching materials 16a, 16b may vary largely from the temperature (of the acoustic matching materials) in the preparing step due to the effect of the temperature of the sample itself. In such a case, the speed of sound in the acoustic matching materials will be different in the preparing step and measuring step. In this case, therefore, the propagation time of the ultrasound measured in the preparing step cannot be considered as the time taken for the wave to travel through the layers of acoustic matching material in the measuring step.

Figure 7:
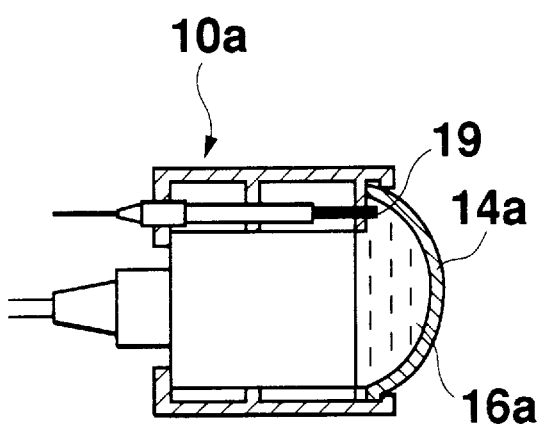
FIG. 7 is a schematic view showing the structure of a transducer unit having a temperature sensor.

According to the second embodiment, a temperature sensor 19 is provided in the transducer unit 10a to measure the temperature of the acoustic matching material 16a as shown in FIG. 7, and a more accurate speed of sound in the sample tissue is calculated using the measurement result of this sensor 19. Apart from the temperature sensor 19, the construction of the apparatus used in the second embodiment is the same as that shown in FIG. 1 and FIG. 2. The output signal from the temperature sensor 19 is input to the controller 50 of FIG. 2. The controller 50 calculates the temperature of the acoustic matching material 16a from the signal output by the temperature sensor 19, and inputs this temperature to the speed calculation unit 58. The computational step used by the unit 58 in this embodiment will be described hereinafter. This temperature sensor 19 may be provided in at least one of the transducer units 10a, 10b.

Figure 8:
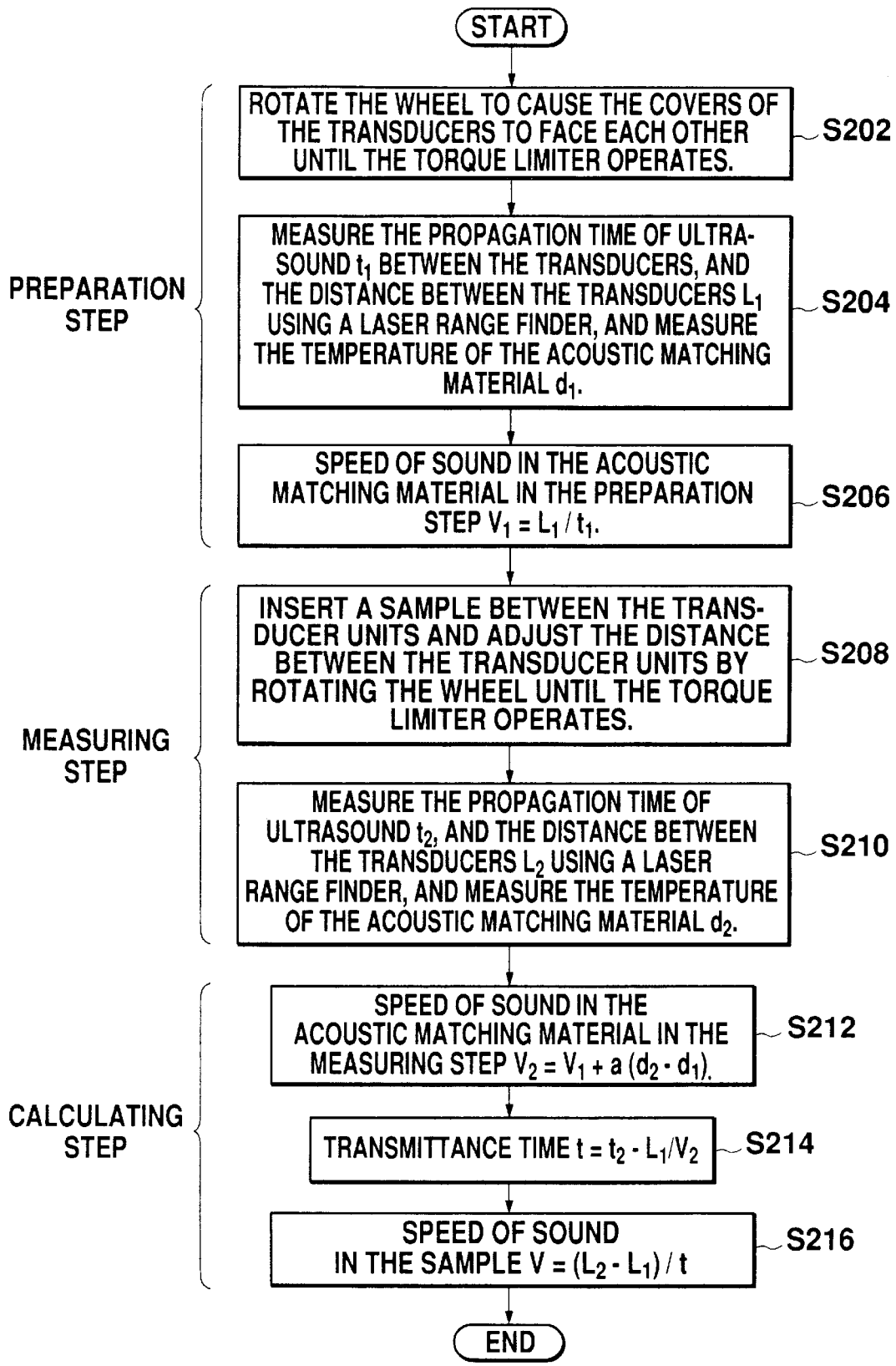
FIG. 8 is a flowchart showing a second embodiment of the method for measuring speed of sound in tissue.

Next, the procedure for measuring the speed of sound in tissue according to the second embodiment will be described with reference to the flowchart of FIG. 8.

First, in the preparing step, the operator turns the wheel 34 until the torque limiter 32 operates so that the transducer covers 14a, 14b of the transducer units 10a and 10b are pressed together with a predetermined pressure (S202). Ultrasound is then transmitted and received so as to measure the propagation time $t_1$ between the transducers, the distance $L_1$ between the transducers is measured by the laser range finder, and the temperature $d_1$ of the acoustic matching material is measured by the temperature sensor 19 (S204).

The speed of sound $V_1$ in the acoustic matching material in the preparing step is then calculated by the following relation (3) (S206):

$$V_1 = L_1/t_1 \tag{3}$$

Next, in the measuring step, the sample 70 is disposed between and held by the transducer units 10a, 10b (S208), and the operator turns the wheel 34 until the torque limiter 32 operates. The propagation time $t_2$ of ultrasound between the transducers 12a, 12b, the distance $L_2$ between the transducers and the temperature $d_2$ of the acoustic matching material are measured (S210).

The speed of sound $V_2$ in the acoustic matching material is then calculated using the following relation (4) (S212):

$$V_2 = V_1 + a(d_2 - d_1) \tag{4}$$

Herein, the constant "a" shows the rate of variation of speed of sound in the acoustic matching material for a 1° C. variation of temperature. The constant "a" is expressed in units of for example m/s·deg. When the acoustic matching material is castor oil, the constant "a" is a value of approximately from −3 to −4.

Next, in the calculation step, the speed of sound in the sample tissue is calculated using the measured values in the preparing step and measuring step, and the speed of sound $V_2$ in the acoustic matching material calculated in the step S212.

For this purpose, the time t required for the ultrasound to travel through the sample tissue is first calculated using the following relation (5):

$$t = t_2 - L_1/V_2 \tag{5}$$

As the distance $L_1$ denotes the thickness of the acoustic matching material, and the speed of sound $V_2$ is the speed of sound in the acoustic matching material in the measuring step, $L_1/V_2$ expresses the time required for the ultrasound to travel through the layers of acoustic matching material in the measuring step. The time required for the ultrasound to travel through the sample tissue alone may be found by subtracting this time ($L_1/V_2$) from the propagation time $t_2$ between the transducers in the measuring step.

The speed of sound V in the sample tissue is then calculated using the following relation (2a) (S216):

$$V = (L_2 - L_1)/t \tag{2a}$$

The speed of sound thus determined is an accurate value corrected for the temperature difference of the acoustic matching material in the preparing step and measuring step.

Embodiment 3

Next, a third embodiment of the method for measuring speed of sound according to this invention will be described.

In the aforesaid first and second embodiments, the transducer covers of the pair of transducer units are brought together in the preparing step, however in this third embodiment, a reference phantom which is as thick as the sample tissue is held between the transducer units, and a measurement made. This reference phantom may for example be an acryl block. The apparatus of this third embodiment is basically of identical construction to that shown in FIG. 1. This embodiment will now be described using the flowchart of FIG. 9.

Figure 10:
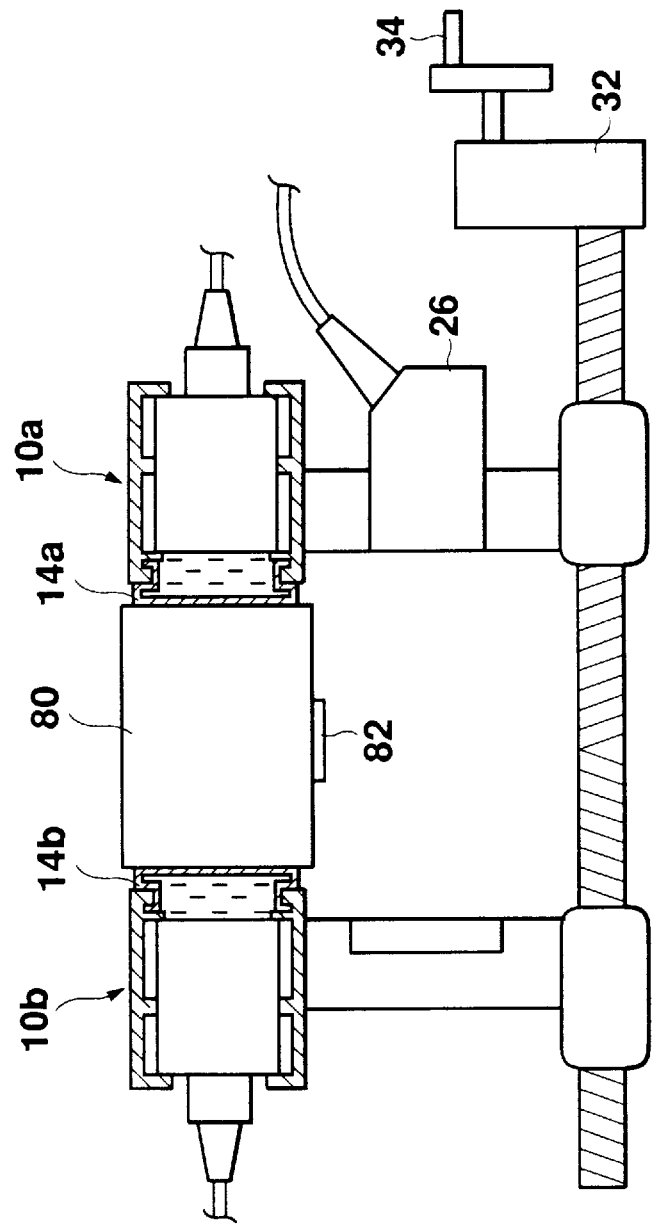
FIG. 10 is an illustrative diagram showing the state of the tissue assessment apparatus in a preparing step according to the third embodiment.

First, in a preparing step, the operator places a reference phantom 80 between the pair of transducer units 10a, 10b. The operator then turns the wheel 34 so as to bring the transducer units closer together and grip the reference phantom 80. The wheel 34 is turned until the torque limiter 32 operates so that the reference phantom 80 is held under a predetermined pressure (S302). FIG. 10 shows the state of the apparatus at this time. In FIG. 10, a temperature sensor 82 for measuring the temperature of the reference phantom 80 is attached to the surface of the phantom 80. The setting of the reference phantom 80 in a predetermined position in the step S302 is automatically performed by a reference phantom setting mechanism, not shown. It will of course be understood that the operator may perform the setting manually himself.

Next, ultrasound is transmitted and received, and the propagation time $t_1$ of the ultrasound between the transducers 12a, 12b is measured. The temperature r (°C.) of the reference phantom 80 at this time is also measured by the temperature sensor 82 (S304).

The speed of sound $V_S$ in the reference phantom 80 in the preparing step is then calculated from the measurement result by the following relation (6) (S306):

$$V_s = \alpha r + \beta \tag{6}$$

In equation (6), $\alpha$ is the temperature gradient of the speed of sound $V_S$ in the reference phantom 80, and $\beta$ is the speed of sound in the reference phantom 80 at a predetermined reference temperature (e.g. 0° C.). Herein, $\alpha$ and $\beta$ are first determined experimentally and stored in the memory 60 (FIG. 2). The speed of sound calculation unit 58 then performs the computation of equation (6) using these constants. The speed of sound $V_S$ thus obtained is temporarily stored in the memory 60.

Next, the operator turns the wheel 34 to temporarily widen the distance between the transducer units 10a, 10b, and removes the reference phantom 80. A sample (i.e. tissue) 70 is then disposed between the transducer units, the wheel 34 is turned until the torque limiter 32 operates, and the sample 70 is held between the transducer units under the aforesaid predetermined pressure (S308).

Ultrasound is then transmitted and received, and the propagation time $t_2$ of the ultrasound is measured. The distance $L_2$ between the transducers at this time is simultaneously measured (S310) by the laser range finder 26.

Next, in the calculating step, the speed of sound $V_S$ in the sample tissue is calculated using the measurement results in the preparing step and measuring step, and the speed of sound $V_S$ in the reference phantom found in S306.

First, the time t required for the ultrasound to travel through the sample alone is calculated using the following relation (7):

$$t = t_2 - \{t_1 - (L_S/V_S)\} \tag{7}$$

In equation (7), $L_S$ is the thickness of the reference phantom 80, and is already known. $L_S/V_S$ therefore expresses the time required for the ultrasound to travel through the reference phantom 80, and $\{t_1-(L_S/V_S)\}$ expresses the time required for the ultrasound to travel through the acoustic matching material. The time t required for the ultrasound to travel through the sample tissue alone may be calculated by subtracting this value from the propagation time $t_2$ of the ultrasound between the transducers.

The speed of sound in the sample tissue may then be calculated by using equation (2) as in the first embodiment:

$$V=L_2/t \tag{2}$$

Hence according to the third embodiment, as in the aforesaid first embodiment, the effect of the propagation time $t_1$ in the acoustic matching material layers is eliminated, so an accurate value of the speed of sound in the sample tissue may be found.

Further, according to this embodiment, the propagation time in the preparation step is measured with the reference phantom 80 which is as thick as the sample tissue held between the transducer units, so the difference of the distances between the transducers in the preparing step and measuring step is less than in the case where the reference phantom 80 is not used (e.g. the first embodiment). According to this embodiment, therefore, the laser range finder 26 may be an economical range finder having a small effective length measurement range, so the apparatus is less costly to manufacture.

Figure 9:
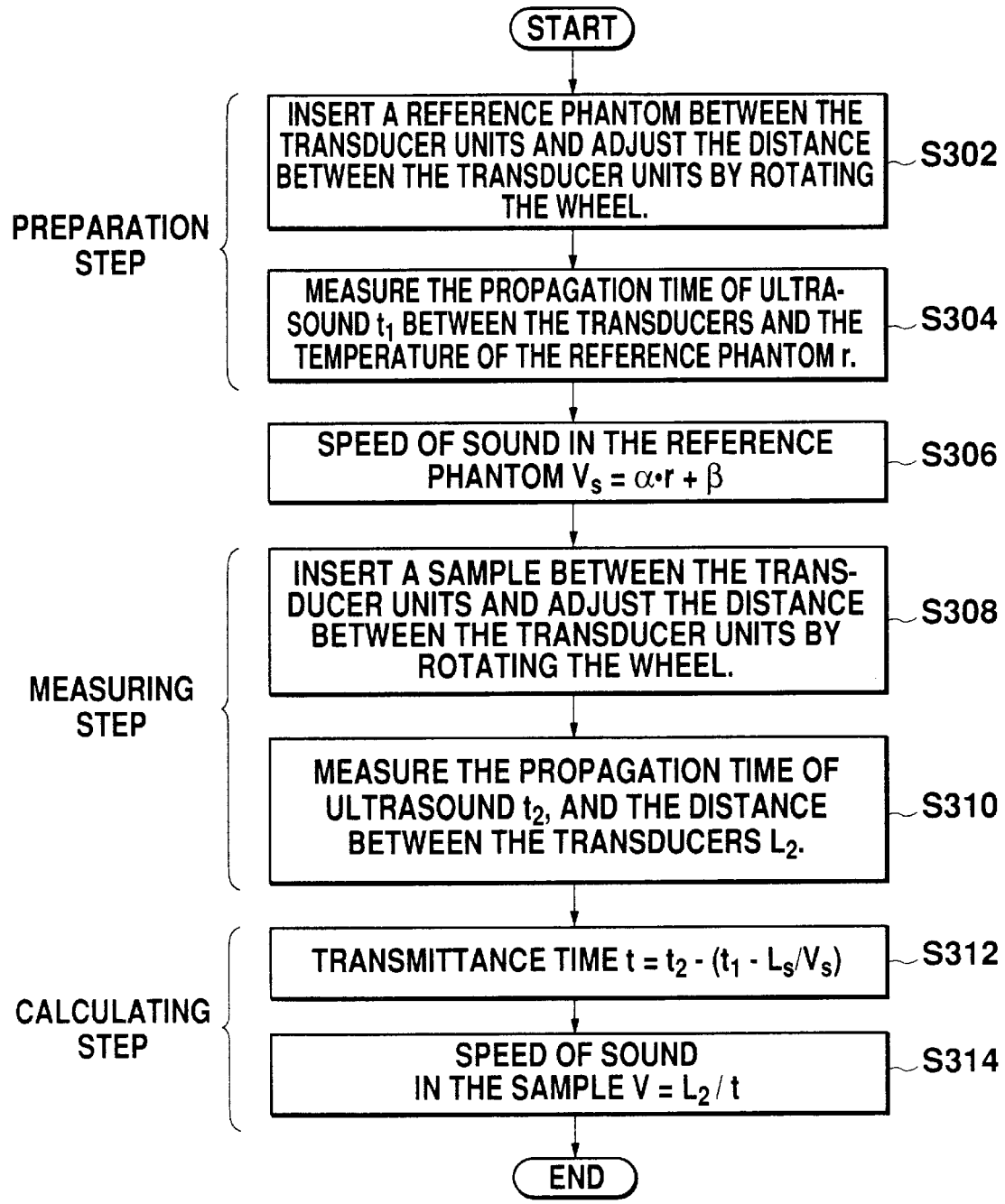
FIG. 9 is a flowchart showing a third embodiment of the method for measuring speed of sound in tissue.
Figure 11:
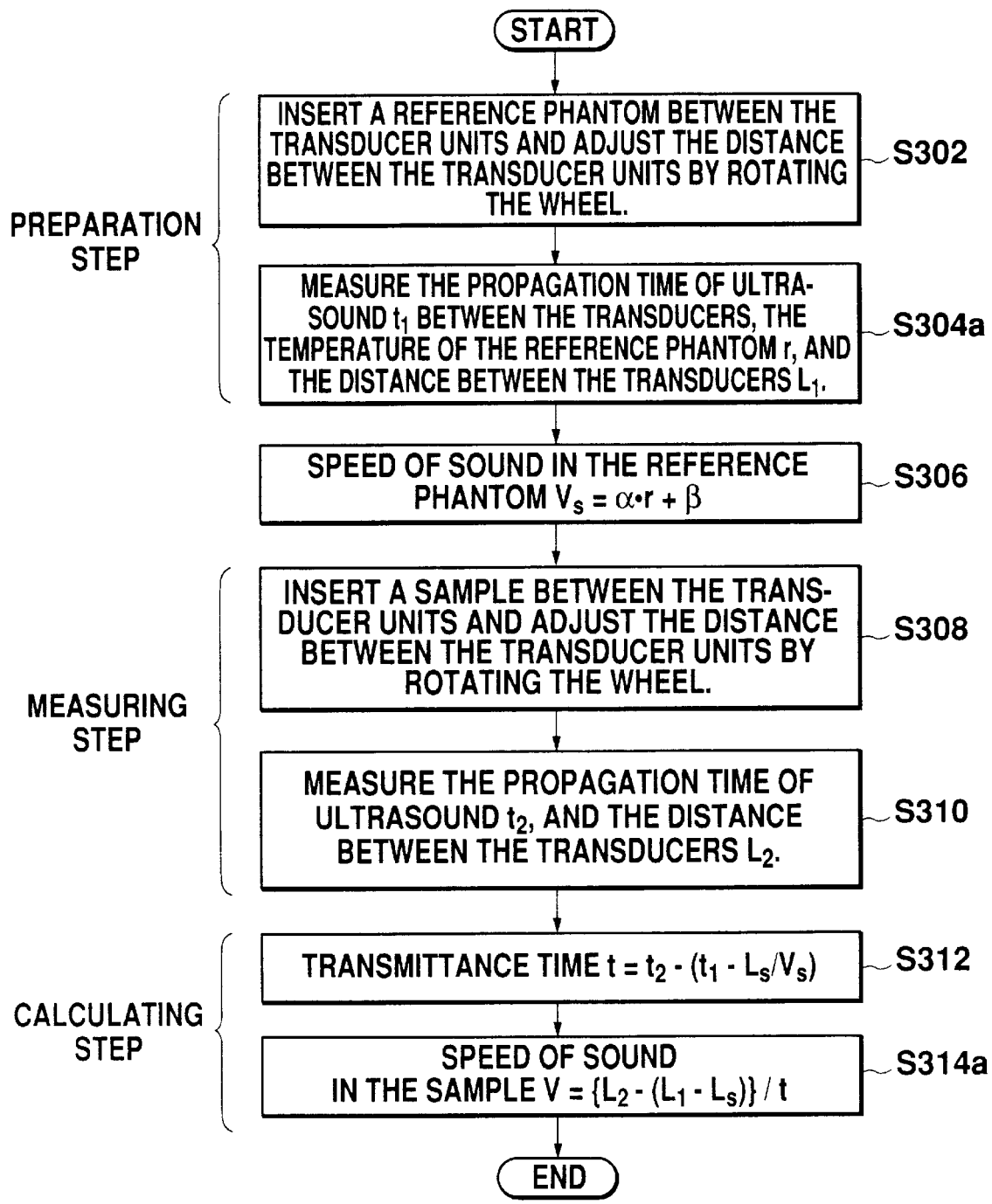
FIG. 11 is a flowchart showing a modification of the third embodiment.

FIG. 11 is a flowchart of the processing performed in this modification of the invention. In FIG. 11, those steps showing the same processing as that of FIG. 9 are assigned the same symbols and their description is omitted. In this modification, in the preparing step, in addition to the propagation time $t_1$ and reference phantom temperature r (°C.), the distance $L_1$ between the transducers is measured by the laser range finder 26 (S304a). In the calculating step, the speed of sound V in the sample tissue is then calculated using the following relation (8) (S314a):

$$V=\{L_2-(L_1-L_S)\}/t \tag{8}$$

Herein, $(L_1-L_S)$ denotes the thickness of the acoustic matching material layer. The thickness of the sample tissue alone may be calculated by subtracting $(L_1-L_S)$ from $L_2$, and by dividing the result by the time t required for the ultrasound to travel through the sample tissue alone, a more accurate value for the speed of sound V in the sample tissue may be calculated.

In this modification, the effect of the acoustic matching material layers has been completely eliminated from the calculation of speed of sound. Consequently, an accurate value for the speed of sound V, unaffected by variations of speed of sound in the acoustic matching material and variations of thickness of the layers of acoustic matching material, may be obtained.

Embodiment 4

Figure 12:
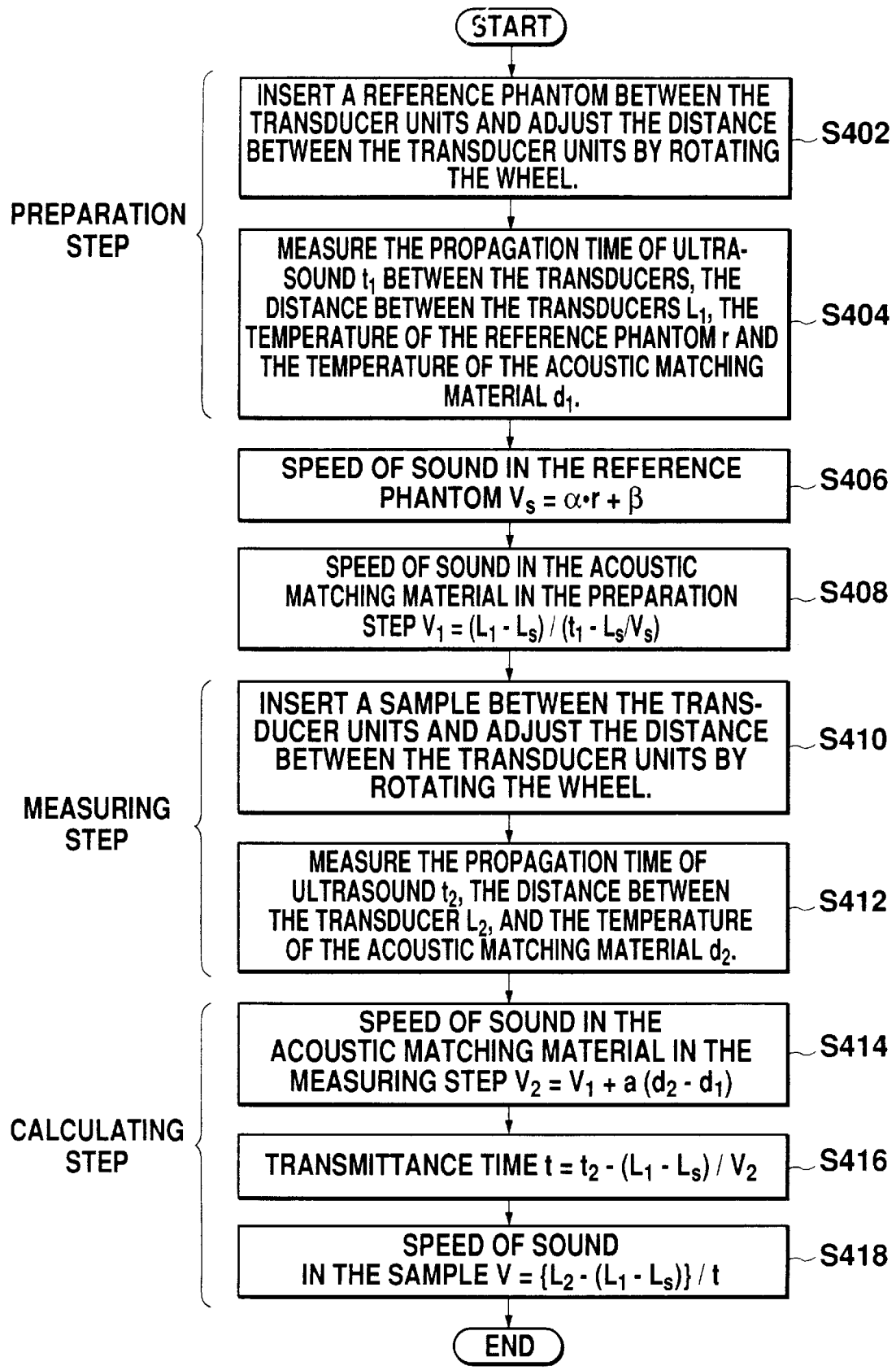
FIG. 12 is a flowchart showing a fourth embodiment of the method for measuring speed of sound in tissue.

Next, a fourth embodiment of the method of measuring speed of sound in tissue according to this invention, will be described. This fourth embodiment is an improvement of the third embodiment described hereinabove, and aims to find a still more accurate value for speed of sound in tissue by considering the temperature variation of the acoustic matching material 16a, 16b. The temperature of the acoustic matching material may be measured by the temperature sensor 19 mentioned in the second embodiment. This embodiment will now be described using the flowchart of FIG. 12.

First, the operator holds the reference phantom 80 by the pair of transducer units (S402). The operator turns the wheel 34 until the torque limiter 32 operates so that the reference phantom 80 is held under a predetermined pressure. The propagation time $t_1$ of ultrasound, the distance $L_1$ between the transducers and the reference phantom temperature r are measured, and the temperature d of the acoustic matching material 16a is measured by the temperature sensor 19 (S404).

The speed of sound $V_S$ in the reference phantom is calculated from these measurement results using equation (6) (S406):

$$V_S=\alpha r+\beta \tag{6}$$

The speed $V_1$ of sound in the acoustic matching material in the preparing step is then calculated from the speed of sound $V_S$ in the reference phantom using the following equation (9) (S408):

$$V_1=(L_1-L_S)/(t_1-L_S/V_S) \tag{9}$$

Next, the operator removes the reference phantom 80 from the space between the transducer units, and replaces it with the sample 70. The operator turns the wheel 34 until the torque limiter 32 operates so that the sample 70 is held between the transducer units under a predetermined pressure (S410). Ultrasound is transmitted and received, the propagation time $t_2$ of the ultrasound is measured, and the temperature $d_2$ of the acoustic matching material and distance $L_2$ between the transducers are measured (S412).

Next, the speed of sound $V_2$ in the acoustic matching material in the measuring step is calculated from these measured values by the following relation (4) (S414):

$$V_2=V_1+a(d_2-d_1) \tag{4}$$

The time t required for the ultrasound to travel through the sample tissue is calculated according to the relation (10):

$$t=t_2-(L_1-L_S)/V_2 \tag{10}$$

$(L_1-L_S)$ is the thickness of the acoustic matching material, so the value $(L_1-L_S)/V_2$ obtained by dividing $(L_1-L_S)$ by the speed of sound $V_2$ of the acoustic matching material in the measuring step is the time required for the ultrasound to travel through the layers of acoustic matching material in the measuring step. The time t required for the ultrasound to travel through the sample tissue alone can therefore be calculated by subtracting this time $(L_1-L_2)/V_2$ from the propagation time $t_2$ of the ultrasound from the transducer 12a to the transducer 12b.

The speed of sound V in the sample tissue can be calculated from this time t by equation (8) as in the third embodiment (S418):

$$V=\{L_2-(L_1-L_S)\}/t \tag{8}$$

According also to the fourth embodiment, therefore, by using the reference phantom 80, a laser range finder having a small effective wavelength measurement range may be used, and the apparatus is less costly to manufacture.

According to the aforesaid third and fourth embodiments, examples were described wherein the reference phantom temperature sensor 82 was attached to the surface of the reference phantom 80, however the invention is not limited to this arrangement since the temperature of the reference phantom 80 may be considered as equal to the room temperature at that time. Further, the temperature measurement of the reference phantom and temperature measurement of the acoustic matching material may be performed by one sensor.

As described hereinabove, according to this invention, an accurate value of the speed of sound in sample tissue, unaffected by changes in the state of the acoustic matching material due to variations of environmental conditions or temporal or other variations of the acoustic matching material layer, may be obtained. In addition, other assessment values apart from speed of sound may be corrected using the accurate speed of sound in tissue found as described hereinabove.

According to this invention, the value obtained for the speed of sound in the sample tissue can be calculated even more accurately by correcting errors due to differences of the temperature of the acoustic matching material in the preparing step and measuring step. According to this invention, the speed of sound in the sample tissue can be accurately calculated even if the temperature of the sample is transmitted to the acoustic matching material in the measuring step so that the temperature of the acoustic matching material varies.

According to this embodiment moreover, by holding a reference phantom which is as thick as the sample between the transducers instead of bringing the pair of transducer units into direct contact in the preparing step, a laser range finder having a small effective length measurement range may be used and the apparatus is therefore less costly.

What is claimed:

1. A tissue assessment apparatus for evaluating tissue by using ultrasound, comprising:

at least one transducer unit for transmitting and/or receiving the ultrasound; and a transducer unit moving mechanism for moving said at least one transducer unit, said transducer unit moving mechanism including limiting means for stopping the movement of said at least one transducer unit when a force applied to said at least one transducer unit reaches a predetermined value and maintaining the stop condition, wherein said limiting means limits both forward and backward movement of said at least one transducer unit while the stop condition is maintained and maintains the stop condition of said at least one transducer unit when a counterforce in excess of said applied force is applied so as to urge said at least one transducer unit backwards with respect to said movement.

2. An apparatus according to claim 1, wherein said limiting means includes a torque limiter.

3. An apparatus according to claim 1, wherein the ultrasound is transmitted and/or received while the stop condition is maintained.

4. A tissue assessment apparatus for evaluating tissue by using ultrasound, comprising:

a pair of transducer units for transmitting and/or receiving the ultrasound; and a transducer unit moving mechanism for changing the distance between said pair of transducer units, said transducer unit moving mechanism including:

drive force generating means for generating a drive force;

a feed screw which is rotated by the drive force from said drive force generating means to move said pair of transducer units; and a torque limiter provided between said drive force generating means and said feed screw, wherein said feed screw includes two parts each having a different direction of thread, one of said two parts being engaged with a nut for supporting one of said pair of transducer units while the other of said parts is engaged with another nut for supporting the other one of said pair of transducer units, and wherein said pair of transducer units move closer to each other when said feed screw rotates in one direction while said pair of transducer units move away from each other when said feed screw rotates in the other direction.

5. An apparatus according to claim 4, wherein said torque limiter limits said drive force transmitted to the feed screw from the drive force generating means so that the drive force is equal to or less than a predetermined value.

* * * * *